United States Patent
Choo et al.

(10) Patent No.: US 10,486,080 B2
(45) Date of Patent: Nov. 26, 2019

(54) DISTILLATION DEVICE

(71) Applicant: LG CHEM, LTD., Seoul (KR)

(72) Inventors: Yeon Uk Choo, Daejeon (KR); Sung Kyu Lee, Daejeon (KR); Tae Woo Kim, Daejeon (KR); Jong Suh Park, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 3 days.

(21) Appl. No.: 15/580,393

(22) PCT Filed: Jul. 1, 2016

(86) PCT No.: PCT/KR2016/007106
§ 371 (c)(1),
(2) Date: Dec. 7, 2017

(87) PCT Pub. No.: WO2017/003247
PCT Pub. Date: Jan. 5, 2017

(65) Prior Publication Data
US 2018/0169542 A1    Jun. 21, 2018

(30) Foreign Application Priority Data

Jul. 2, 2015  (KR) .................. 10-2015-0094491

(51) Int. Cl.
*B01D 3/14* (2006.01)
*B01D 3/32* (2006.01)
(Continued)

(52) U.S. Cl.
CPC ............. *B01D 3/143* (2013.01); *B01D 3/141* (2013.01); *B01D 3/32* (2013.01); *B01D 3/36* (2013.01);
(Continued)

(58) Field of Classification Search
CPC .......... B01D 3/141; B01D 3/143; B01D 3/32; B01D 3/36; C07C 37/08; C07C 45/53; C07C 45/84
See application file for complete search history.

(56) References Cited

U.S. PATENT DOCUMENTS

| 5,510,543 A * | 4/1996 | Fulmer ................... C07C 37/72 568/741 |
| 8,242,314 B2 * | 8/2012 | Hahn ..................... B01D 3/146 568/388 |

(Continued)

FOREIGN PATENT DOCUMENTS

| KR | 1019960037630 | 11/1996 |
| KR | 1020070094923 | 9/2007 |

(Continued)

OTHER PUBLICATIONS

Espacenet translation of KR1020130019667 Obtained Mar. 1, 2019. (Year: 2019).*

*Primary Examiner* — Jonathan Miller
(74) *Attorney, Agent, or Firm* — Dentons US LLP

(57) ABSTRACT

The present application relates to a distillation device. When a feedstock containing acetone and methanol is separated using a distillation device according to the present application, a methanol removal distillation column may be located at a position for easily separating methanol to solve a problem due to accumulation of methanol in the process and to lower the methanol content in the acetone product, and thus the lifetime of catalysts can be extended, and moreover, methanol can be removed with good efficiency from a flow of the lower part of the distillation column obtaining the final acetone product by using only the conventional phase separator and one methanol removal distillation column further installed, so that the acetone product obtained from the upper part of the distillation column obtaining the acetone (Continued)

product can be obtained in high purity and the operating cost and the equipment cost of equipments can be greatly reduced.

6 Claims, 7 Drawing Sheets

(51) Int. Cl.
*B01D 3/36* (2006.01)
*C07C 37/08* (2006.01)
*C07C 45/53* (2006.01)
*C07C 45/84* (2006.01)

(52) U.S. Cl.
CPC ............ *C07C 37/08* (2013.01); *C07C 45/53* (2013.01); *C07C 45/84* (2013.01)

(56) References Cited

U.S. PATENT DOCUMENTS

| | | | | |
|---|---|---|---|---|
| 2010/0222612 | A1* | 9/2010 | Hahn | B01D 3/146 568/388 |
| 2013/0144080 | A1* | 6/2013 | Schmidt | C07C 68/08 558/277 |
| 2014/0231240 | A1* | 8/2014 | Wismer | C07C 17/383 203/41 |
| 2015/0152032 | A1* | 6/2015 | Aird | C07B 63/00 203/77 |

FOREIGN PATENT DOCUMENTS

| | | |
|---|---|---|
| KR | 1020080056006 | 6/2008 |
| KR | 1020130019667 | 2/2013 |
| KR | 1020150026127 | 3/2015 |

\* cited by examiner

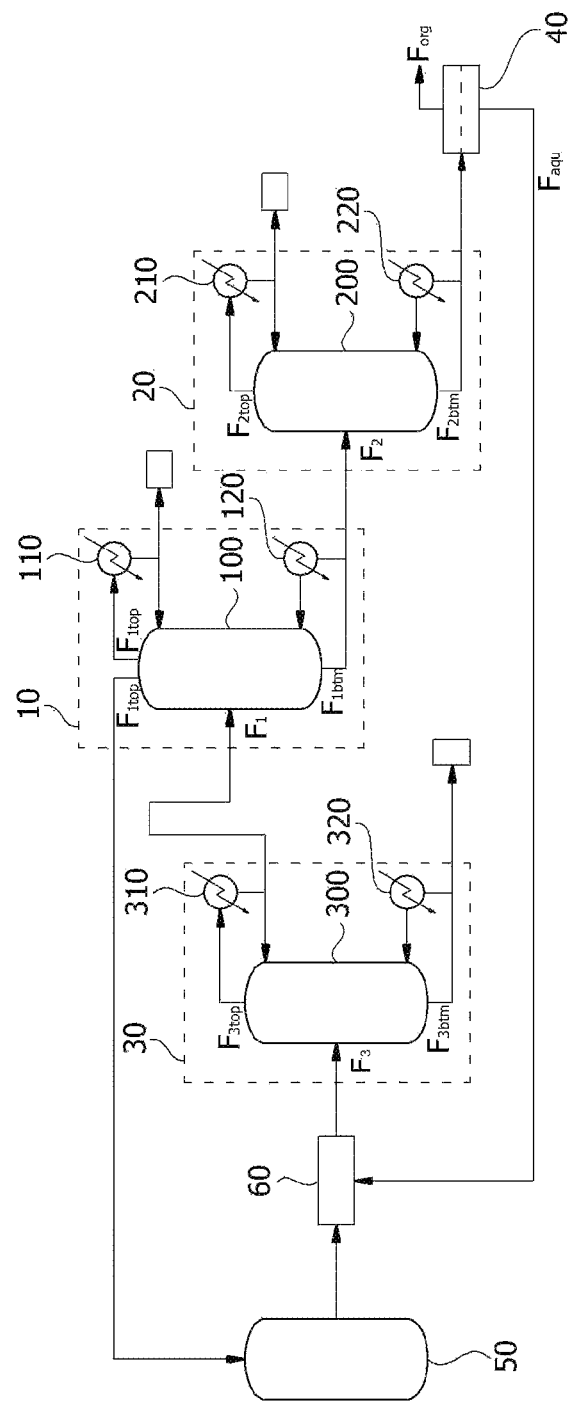
[Figure 1]

[Figure 2]
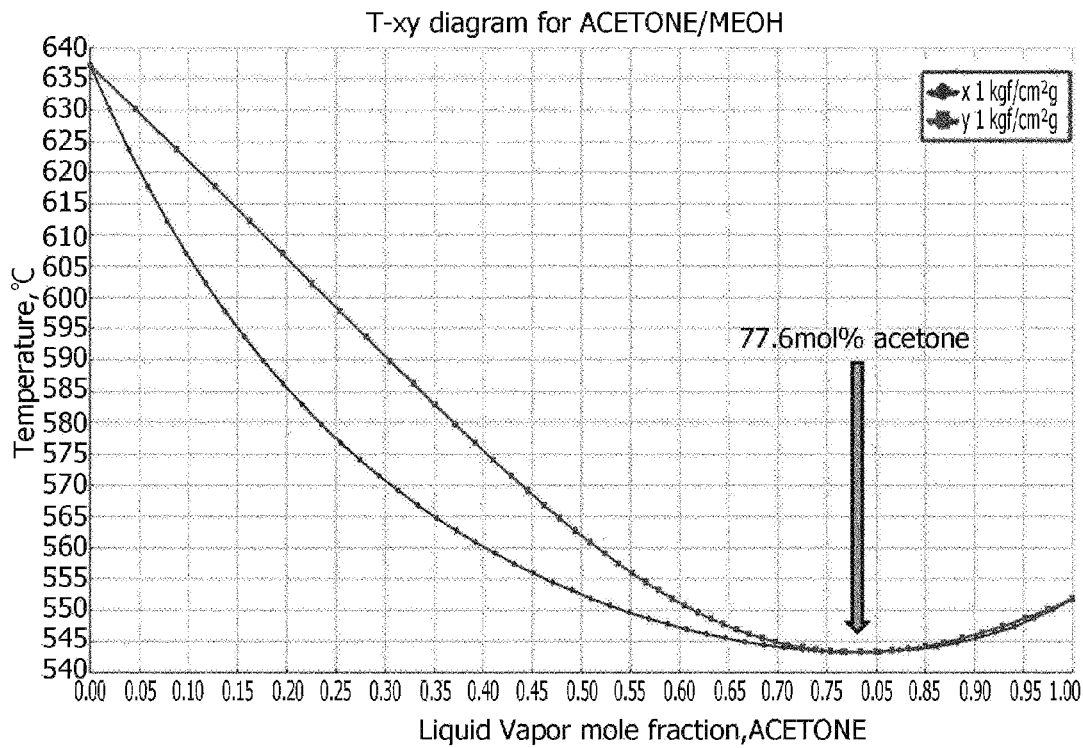
[Figure 3]
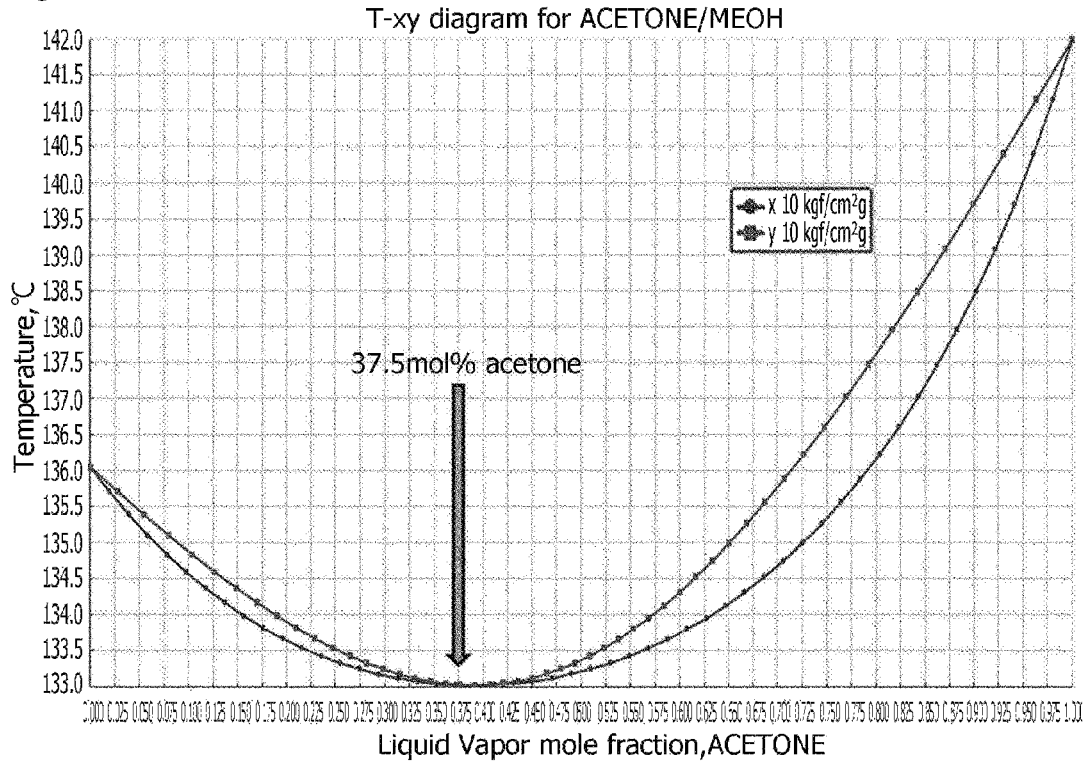

[Figure 4]
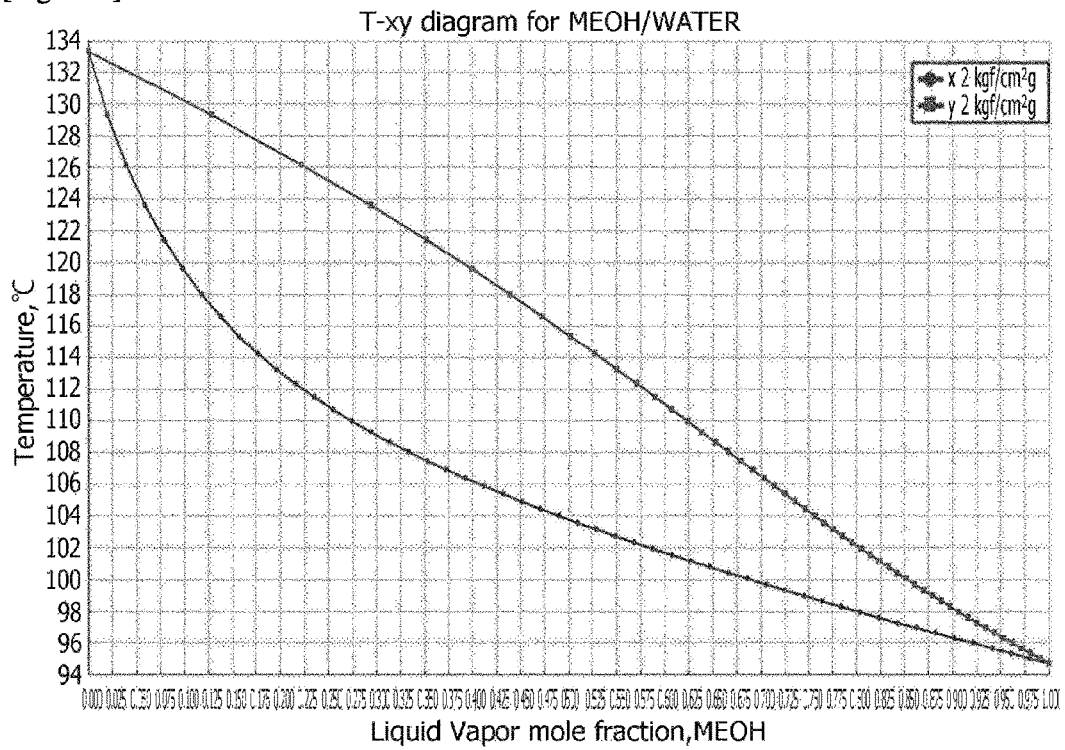
[Figure 5]
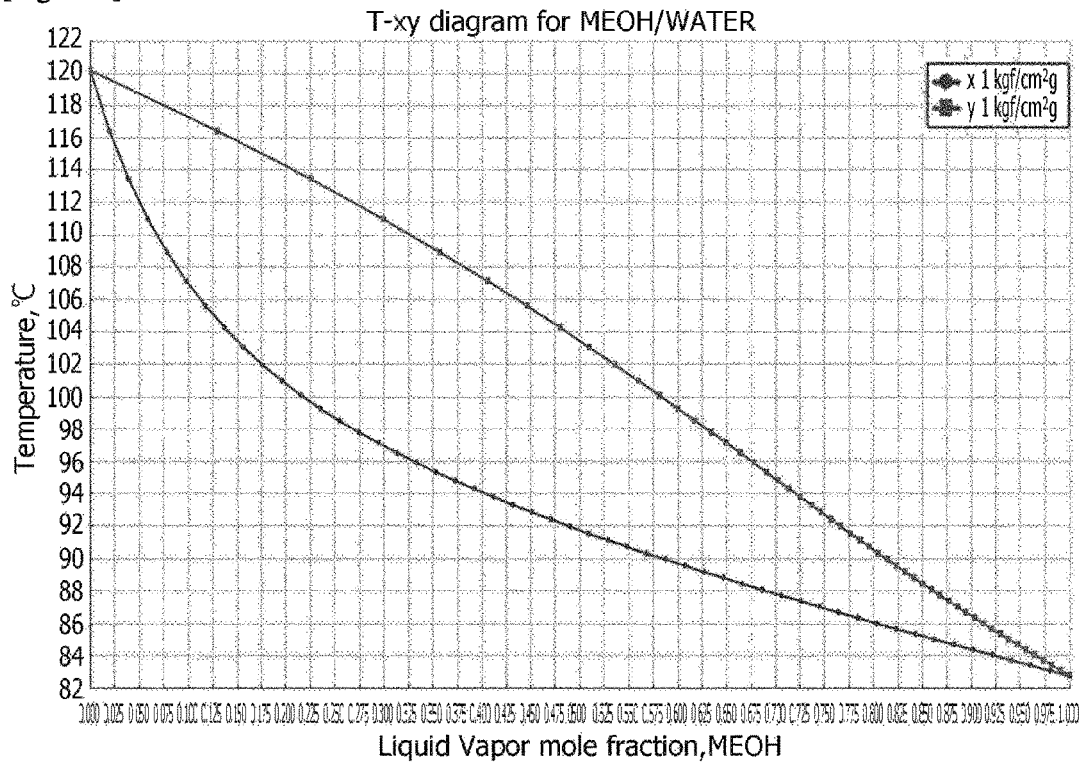

[Figure 6]
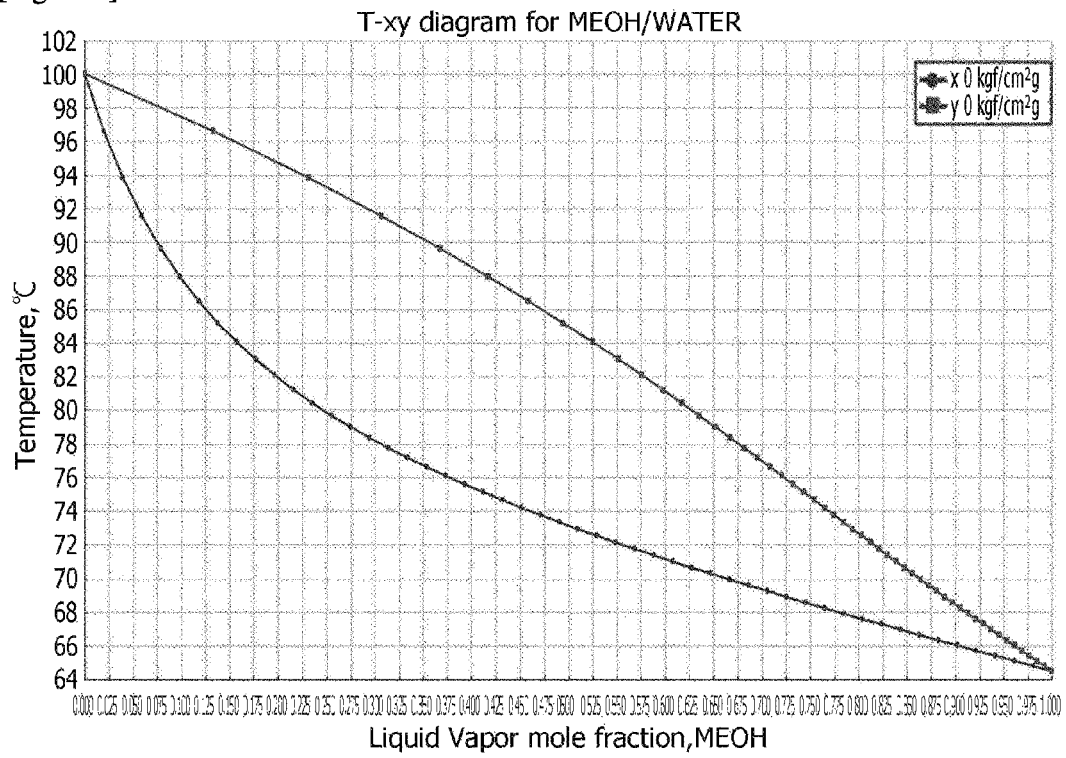
[Figure 7]
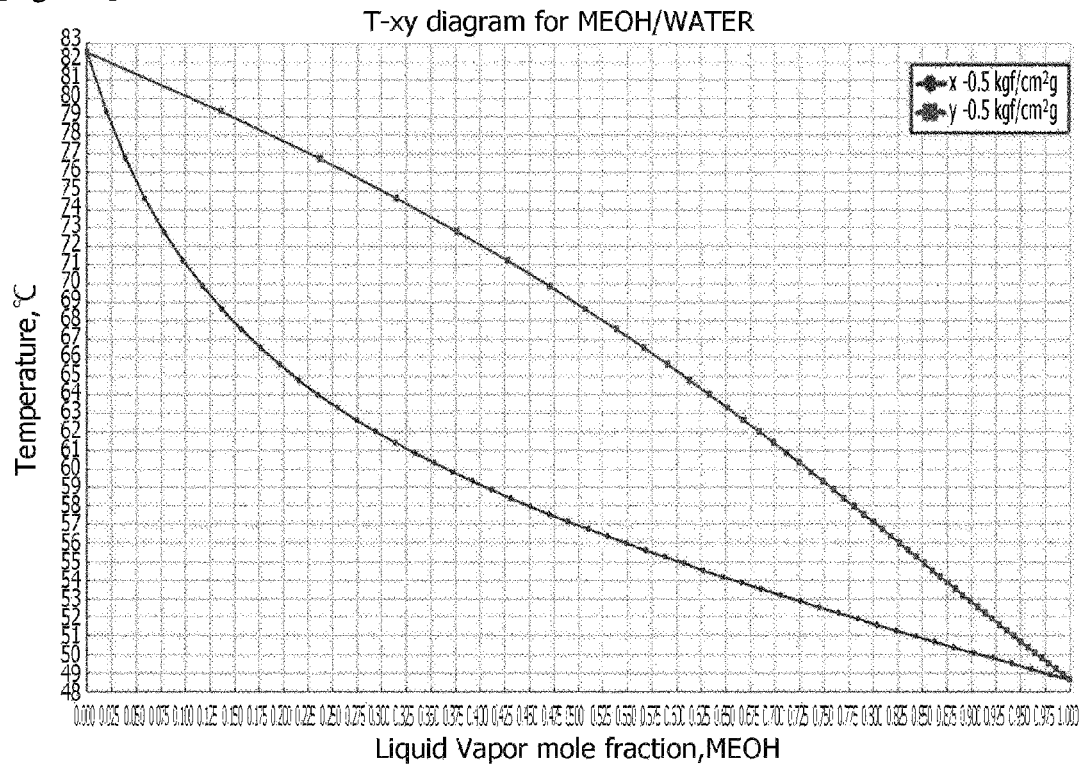

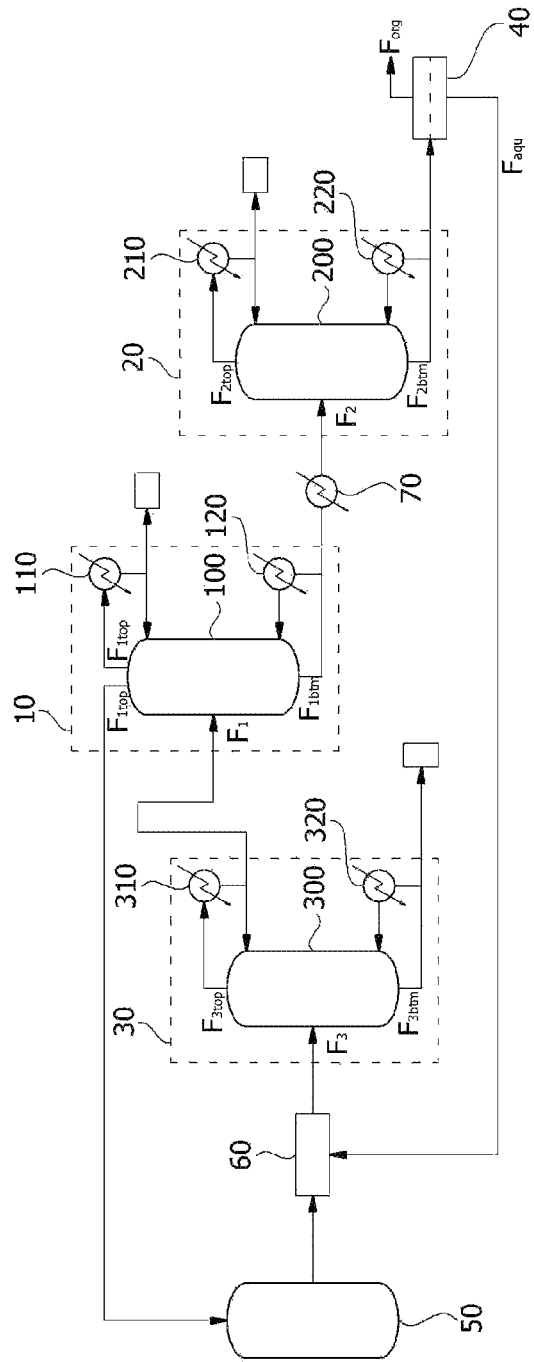
[Figure 8]

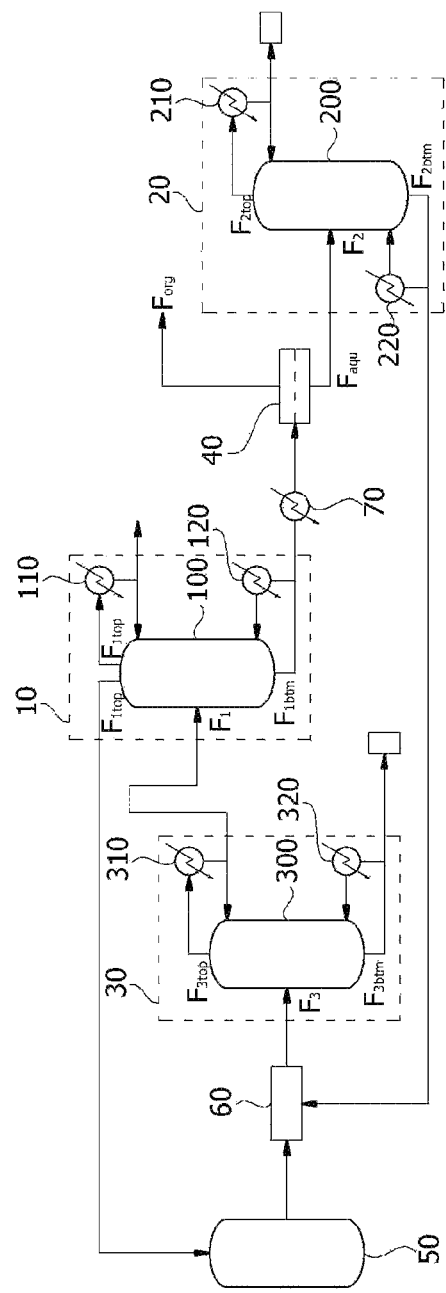
[Figure 9]

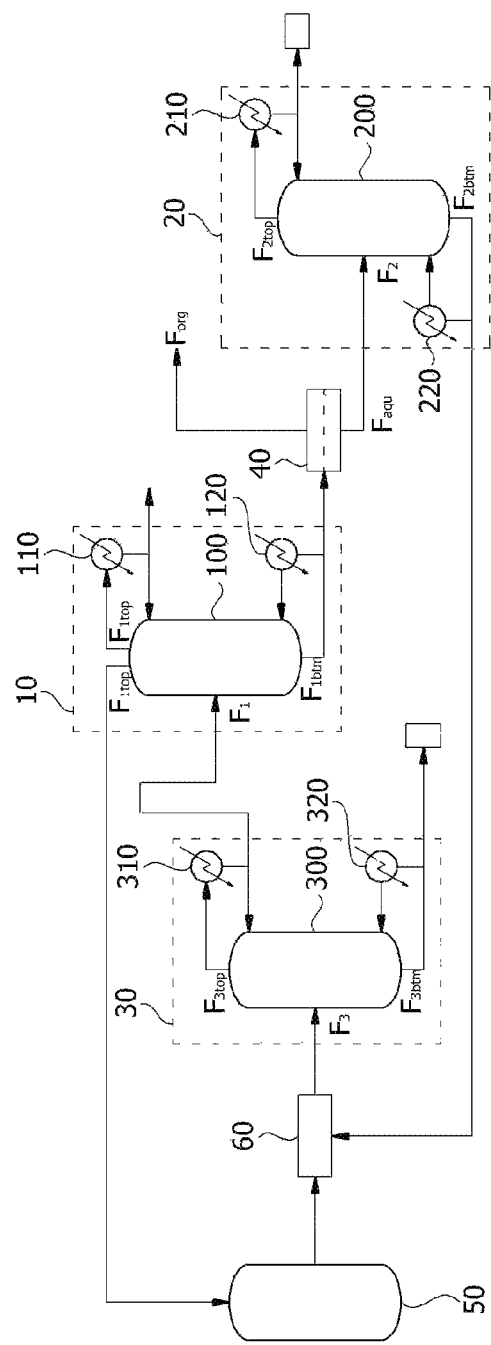
[Figure 10]

DISTILLATION DEVICE

This application is a National Stage Application of International Application No. PCT/KR2016/007106, filed Jul. 1, 2016, and claims the benefit of Korean Patent Application No. 10-2015-00944191, filed Jul. 2, 2015, contents of which are incorporated herein by reference in their entirety for all purposes as if fully set forth below.

TECHNICAL FIELD

The present application relates to a distillation device.

BACKGROUND ART

Phenol is used in various fields as feedstocks of various synthetic resins such as polycarbonate resin and epoxy resin, including phenol resin, or feedstocks in the pharmaceutical industry, and feedstocks of detergents, such as nonylphenol, or various color paints.

Methods for producing phenol from cumene are well known. For example, the cumene is oxidized using a gas containing oxygen to form cumene hydroperoxide, which is again decomposed under an acidic catalyst, thereby resulting in phenol and acetone.

In the process of generating phenol as above, various side reactions occur at the same time. For example, a trace amount of methanol is generated in the reaction process and included in the acetone product, and the methanol may act as a catalyst poison on BPA reaction of acetone to shorten the lifetime of the catalyst.

Meanwhile, it has been known that it is relatively difficult to separate acetone and methanol, and conventionally, methods have been used, such as a pressure swing distillation process (PSD) for separating highly pure methanol at a pressure of about 1 $kgf/cm^2g$ through change of an operating pressure and separating highly pure acetone at a pressure of 10 $kgf/cm^2g$ or an extractive distillation process for separating methanol and acetone by means of water having an excellent affinity with methanol as a solvent. However, since the mixture of acetone and methanol forms an azeotrope and the boiling point is reversed at each pressure of 1 $kgf/cm^2g$ and 10 $kgf/cm^2g$, at least two or more separation and purification columns were required to separate them and thus there was a problem that the operating cost and the equipment cost of equipments are greatly increased.

Therefore, a distillation method for separating the methanol more effectively is required.

DISCLOSURE

Technical Problem

The present application is intended to provide a distillation device which separates methanol and acetone at low cost and high purity.

Technical Solution

One embodiment of the present application provides a distillation device. According to an exemplary distillation device of the present application, when a feedstock containing acetone and methanol is separated using a distillation device, a methanol removal distillation column may be located at a position for easily separating methanol to solve a problem due to accumulation of methanol in the process and to lower the methanol content in the acetone product, and thus the lifetime of catalysts can be extended. Furthermore, methanol can be removed with good efficiency from a flow of the lower part of the distillation column obtaining the final acetone product by using only the conventional phase separator and one methanol removal distillation column further installed, so that the acetone product obtained from the upper part of the distillation column obtaining the acetone product can be obtained in high purity and the operating cost and the equipment cost of equipments can be greatly reduced.

Hereinafter, a distillation device of the present application will be described with reference to the attached drawings, but the attached drawings are illustrative, and the distillation device of the present application is not limited by the attached drawings.

FIG. 1 is a diagram schematically showing a distillation device according to one embodiment of the present application.

As in FIG. 1, the distillation device of the present application comprises at least one or more distillation units. The term "distillation unit" above means one unit body which comprises a distillation column and a condenser and a reboiler, connected to the distillation column, respectively, and can perform distillation processes.

The distillation column is a device being capable of separating multi-component materials contained in feedstocks by each boiling point difference. Distillation columns having various shapes can be used in the distillation device of the present application in consideration of boiling points of components of the introduced feedstocks or components to be separated. The specific type of the distillation column which can be used in the distillation device of the present application is not particularly limited, and for example, a distillation column having a general structure as shown in FIG. 1 or a dividing wall distillation column equipped with a dividing wall inside may be also used. In one example, the distillation column can be divided into an upper region and a lower region. The term "upper region" herein may mean a relatively upper portion in the structure of the distillation column, and for example, mean the uppermost portion of the divided two regions when the distillation column is divided into two portions in the height direction or the longitudinal direction of the distillation column. In addition, the above "lower region" may mean a relatively lower portion in the distillation column structure, and for example, mean the downmost portion of the divided two regions when the distillation column is divided into two portions in the height direction or the longitudinal direction of the distillation column. Herein, the upper region and the lower region of the distillation column can be used in a relative concept to each other. The top of the distillation column is included in the upper region and the bottom of the distillation column is included in the lower region; however, unless otherwise defined herein, the upper region is used in the same sense as the top region and the lower region is used in the same sense as the bottom region. As the distillation column, a distillation column having a number of theoretical stages of 15 to 45 can be used. In the above, the "number of theoretical stages" means a number of imaginary regions or stages in which two phases such as a vapor phase and a liquid phase in the distillation column are in equilibrium with each other.

In one embodiment, as in FIG. 1, the first distillation unit (10) comprises a first distillation column (100), and a first condenser (110) and a first reboiler (120), connected to the first distillation column (100), respectively. For example, the first distillation column (100), the first condenser (110), and the first reboiler (120) may be fluidically connected to each other so that the fluid introduced into the first distillation column (100) can flow. The "condenser" above is a device separately installed outside the distillation column, and means a device for cooling the flow discharged from the top of the distillation column by a method such as contacting it with cooling water introduced outside. For example, the first condenser (110) of the first distillation column (100) is a device for condensing a first top flow ($F_{1top}$) discharged from the top region of the first distillation column (100), and a second condenser (210) and a third condenser (310) of a second distillation column (200) and a third distillation column (300), which are described below, may be devices for condensing a second top flow ($F_{2top}$) discharged from the top region of the second distillation column (200) and a third top flow ($F_{3top}$) discharged from the top region of the third distillation column (300). In addition, the reboiler" above may be a heating device separately installed outside the distillation column and mean a device for again heating and evaporating a flow of high-boiling components discharged from the bottom of the distillation column. For example, the first reboiler (120) of the first distillation column (100) is a device for heating a bottom flow discharged from the bottom region of the first distillation column (100), and a second reboiler (220) of the second distillation column and a third reboiler (320) of the third distillation column (300), which are described below, may be devices for heating a second bottom flow discharged from the bottom region of the second distillation column (200) and a third bottom flow ($F_{3btm}$) discharged from the bottom region of the distillation column (300).

As shown in FIG. 1, the distillation device according to one embodiment of the present application comprises a first distillation unit (10) comprising a first distillation column (100), a phase separator (40), and a second distillation unit (20) located between the distillation column (100) and the phase separator (40) and comprising a second distillation column (200) fluidically connected to the first distillation column (100) and the phase separator (40).

In one example, a feedstock ($F_1$) comprising a first compound, a second compound and water flows into the first distillation column (100).

The first compound and the second compound are not particularly limited as long as they are mixed with each other to form an azeotrope. The term "azeotrope" above means a liquid mixture in a solution state in which azeotropy or the like may occur. Generally, if a solution is distilled, the composition changes according to boiling, with usually raising or lowering the boiling point as well, but a certain type liquid having a special ratio of components boils without changing the ratio of components at a certain temperature like a pure liquid, where the ratios of components in solution and vapor become same, and then the system is referred to as being in an azeotropic state, the ratio of components is referred to as an azeotropic composition, the solution is referred to as an azeotrope and the boiling point of the azeotrope is referred to as an azeotropic point. In one example, the first compound may be acetone, and the second compound being capable of forming an azeotrope with the acetone may be methanol, without being particularly limited thereto. The water contained in the feedstock is an example of an entrainer or a third component capable of breaking the azeotropic point of the azeotrope by azeotropically distilling the azeotrope, and the water may increase a relative volatility of methanol more than that of acetone to facilitate separation of the azeotrope of methanol and acetone.

FIG. 2 is a Txy diagram of a mixture of acetone and methanol under a pressure of 1 kgf/cm$^2$g, and FIG. 3 is a Txy diagram of a mixture of acetone and methanol at a pressure of 10 kgf/cm$^2$g. In the above diagrams, the vertical axis represents the temperature, and the horizontal axis represents the mole fraction (x) of a liquid phase composition or the mole fraction (y) of a vapor phase composition. As can be seen from FIGS. 2 and 3, the mixture of acetone and methanol has a boiling point reversed at each pressure of 1 kgf/cm$^2$g and 10 kgf/cm$^2$g to form an azeotrope, in which general separation and purification can be difficult, and thus at least two distillation columns are required to separate it. FIGS. 4 to 7 are Txy diagrams of a mixture of water and methanol under each pressure of 2 kgf/cm$^2$g, 1 kgf/cm$^2$g, 0 kgf/cm$^2$g and −0.5 kgf/cm$^2$g. As shown in FIGS. 4 to 7, the mixture of methanol and water has the boiling points with no overlap to be easily separated, so that methanol can be removed even if only one distillation column is used. In the present application, using characteristics of such a binary mixture of water and methanol, the feedstock comprising the first compound and the second compound, which are capable of forming an azeotrope with each other, and water being capable of azeotropically distilling the azeotrope is introduced into the methanol removal distillation column further installed before phase separation, and thus methanol and acetone can be separated at low cost and high efficiency.

In one example, the feedstock ($F_1$) containing the first and second compounds and water introduced into the first distillation column (100) is divided into the first top flow ($F_{1top}$) discharged from the top region of the first distillation column (100) and the first bottom flow ($F_{1btm}$) discharged from the bottom region of the first distillation column (100), respectively, and discharged. The first top flow ($F_{1top}$) discharged from the top region of the first distillation column (100) flows into the first condenser (110) and some or all of the first top flow ($F_{1top}$) passing through the first condenser (110) may be refluxed to the top region of the first distillation column (100) or stored as a product. In one example, a flow discharged from the first condenser (110) may be refluxed to the first distillation column (100) or stored as a product after being introduced into a storage tank and stored. In addition, a portion of the first bottom flow ($F_{1btm}$) discharged from the bottom region of the first distillation column (100) flows into the first reboiler (120), and a portion of the bottom flow ($F_{1btm}$) passing through the first reboiler (120) may be refluxed to the bottom region of the first distillation column (100) and the remaining portion may flow into the second distillation column (200).

In one embodiment, the first top flow ($F_{1top}$) comprises a relatively low boiling point component of the feedstock ($F_1$) components introduced into the first distillation column (100), and in one example, it comprises the first compound and the second compound. Also, the first bottom flow ($F_{1btm}$) comprises a relatively high boiling point component among the components contained in the feedstock introduced into the first distillation column (100), and in one example, it comprises the first compound, the second compound and a substance having a boiling point higher than that of the second compound. In one example, as described above, the first compound may be acetone, where the second compound may be methanol and the substance having a boiling point higher than that of the second compound may be one or more selected from the group consisting of aliphatic aldehyde, alpha-methylstyrene, mesityl oxide and cumene, without being limited thereto. In one embodiment, when the boiling point of the second compound is higher than that of the first compound, the first top flow ($F_{1top}$) may be a flow that a concentration of the first compound is relatively higher than that of the second compound and the first bottom flow ($F_{1btm}$) may be a flow that the concentration of the first compound is relatively lower than that of the second compound.

The remaining portion of the first bottom flow ($F_{1btm}$) discharged from the bottom region of the first distillation column (100) may flow into the second distillation column (200). In addition, a flow ($F_2$) introduced into the second distillation column (200) may be divided into the second top flow ($F_{2top}$) discharged from the top region of the second distillation column (200) and the second bottom flow ($F_{2btm}$) discharged from the bottom region of the second distillation column (200), respectively, and discharged.

The second top flow ($F_{2top}$) discharged from the top region of the second distillation column (200) flows into the second condenser (210) and some or all of the second top flow ($F_{2top}$) passing through the second condenser (210) may be refluxed to the top region of the second distillation column (200) or stored as a product. In one example, the flow discharged from the second condenser (210) may be refluxed to the second distillation column (200) or stored as a product after being introduced into the storage tank and stored. In addition, a portion of the second bottom flow ($F_{2btm}$) discharged from the bottom region of the second distillation column (200) flows into the second reboiler (220), and a portion of the second bottom flow ($F_{2btm}$) passing through the second reboiler (220) may be refluxed to the bottom region of the second distillation column (200) and the remaining portion may flow into the phase separator (40) to be described below.

The second top flow ($F_{2top}$) comprises relatively low boiling point components, for example, the first compound and the second compound, among the components contained in the first bottom flow ($F_{1btm}$) introduced into the second distillation column (200), and in one example, it may comprise one or more selected from the group consisting of acetone, methanol and water, but is not limited thereto. Also, the second bottom flow ($F_{2btm}$) comprises relatively high boiling point components, for example, a substance having a boiling point higher than that of the second compound, among the components contained in the first bottom flow ($F_{1btm}$) introduced into the second distillation column (200), and in one example, it may comprise one or more selected from the group consisting of water, aliphatic aldehyde, alpha-methylstyrene, cumene and mesityl oxide, but is not limited thereto. In one embodiment, when the boiling point of the second compound is higher than that of the first compound, since most of the first compound is separated as the first top flow ($F_{1top}$) of the first distillation column (100), the second top flow ($F_{2top}$) may be a flow with a high concentration of the second compound and may also comprise a small amount of the first compound. Also, the second bottom flow ($F_{2btm}$) may be a flow having a higher concentration of the substance having a boiling point higher than that of the second compound and may comprise a small amount of the first compound and the second compound.

The remaining portion of the second bottom flow ($F_{2btm}$) comprising the first compound, the second compound and the substance having a boiling point higher than that of the second compound may flow into the phase separator. A flow introduced into the phase separator (40) may be phase separated in the phase separator (40), and in one example, it may be divided into an organic substance-containing component ($F_{org}$) and a water-containing component ($F_{aqu}$), respectively, and discharged. The organic substance-containing component ($F_{org}$) may comprise an organic component such as, for example, aliphatic aldehyde, alpha-methylstyrene, mesityl oxide or cumene as the remaining components, other than water, among the substances having a boiling point higher than that of the second compound, and the water-containing component ($F_{aqu}$) comprises water and may comprise a first compound and a second compound, for example, a small amount of acetone and methanol. The water-containing component ($F_{aqu}$) may be circulated to the first distillation column (100) through a neutralizer (60) and a third distillation unit (30), which are described below, and through such a process, the acetone product can be obtained in high purity.

In the distillation device of the present application, as described above, when the second compound is separated from the feedstock ($F_1$) containing the first and second compounds being capable of forming an azeotrope and water, the content of the second compound in a flow discharged from the top of the first distillation column (100) can be minimized by installing the second distillation column (200) at a position for relatively separating the second compound easily, that is, between the first distillation column (100) and the phase separator (40) and separating the second compound from the second distillation column (200), followed by separating the water-containing component ($F_{aqu}$) from the phase separator (40) and circulating it to the first distillation column (100). In one example, the content of the second compound in the first top flow ($F_{1top}$) may be 0.002 to 0.1 parts by weight relative to 100 parts by weight of the total components contained in the first top flow ($F_{1top}$). By controlling the content of the second compound in the first top flow ($F_{1top}$) within the above range, an accumulating amount of the second compound in the process can be minimized, whereby the second compound may be separated in high purity and the energy saving effect may be maximized.

In one example, when the content of the second compound in the first top flow ($F_{1top}$) of the first distillation column (100) is controlled within the above range, the content of the second compound in the second top flow ($F_{2top}$) of the second distillation column (200) may be 0.01 to 0.5 parts by weight relative to 100 parts by weight of the total components contained in the second top flow ($F_{2top}$).

In addition, when the second distillation column (200) is located between the first distillation column (100) and the phase separator (40) as above, other embodiments of the present application provide operating conditions inside the second distillation column (200).

In one example, the temperature of the top region of the second distillation column (200) may be 40° C. to 120° C. Also, in this case, the pressure of the top region of the second distillation column (200) may be −0.6 to 5.5 kgf/cm²g.

The temperature of the bottom region of the second distillation column (200) may be 70° C. to 160° C. In addition, the pressure of the bottom region of the second distillation column (200) may be −0.4 to 5.5 kgf/cm²g. In the above, the unit kgf/cm²g means a gauge pressure.

As in FIG. 1, the distillation device of the present application may further comprise a reactor (50), a neutralizer (60) and a third distillation unit (30), in addition to the first distillation unit (10), the second distillation unit (20) and the phase separator (40) as described above. The third distillation unit (30) comprises a third condenser (310), a third reboiler (320) and a third distillation column (300), and since the contents related to the condenser, the reboiler and the distillation column are the same as described above, they are omitted.

The reactor (50) is a device in which a chemical reaction takes place, and the first compound and the second compound, which are generated as by-products of the chemical reaction, may flow out of the reactor (50). When the reaction occurring in the reactor (50) is, for example, an oxidation reaction of cumene, the first compound may be acetone and the second compound may be methanol. The first compound and the second compound, discharged from the reactor (50), may flow into the neutralizer (60) after being combined with the water-containing component ($F_{aqu}$) separated and discharged from the phase separator (40), for example, the water-containing component ($F_{aqu}$) composed of a small amount of the first and second compounds and most of water.

The neutralizer (60) is a device for neutralizing a feedstock containing the first compound, the second compound and water, in which the neutralization can avoid from corrosion in devices. The flow ($F_3$) of the feedstock discharged after being neutralized in the neutralizer (60) may flow into the third distillation column (300) included in the third distillation unit (30).

In one example, the feedstock ($F_3$) introduced into the third distillation column (300) may be divided into the third top flow ($F_{3top}$) discharged from the top region of the third distillation column (300) and the third bottom flow ($F_{3btm}$) discharged from the bottom region of the third distillation column (300), respectively, and discharged.

The third top flow ($F_{3top}$) discharged from the top region of the third distillation column (300) flows into the third condenser (310), and some or all of the third top flow ($F_{3top}$) passing through the third condenser (310) may be refluxed to the top region of the third distillation column (300) or stored as a product. In one example, the flow discharged from the third condenser (310) may be refluxed to the third distillation column (300) or stored as a product after being introduced into the storage tank and stored. In addition, a portion of the third bottom flow ($F_{3btm}$) discharged from the bottom region of the third distillation column (300) flows into the third reboiler (320), and a portion of the third bottom flow ($F_{3btm}$) passing through the third reboiler (320) may be refluxed to the bottom region of the third distillation column (300) and the remaining portion may flow into the first distillation column (100) described above. Also, in this case, a portion of the first top flow ($F_{1top}$) may be introduced into the reactor (50) and circulated.

In another embodiment, the distillation device of the present application may further comprise a cooling device. FIG. 8 is a diagram schematically showing a distillation device according to an embodiment of the present application.

In one example, as in FIG. 8, the distillation device may further comprise a cooling device (70) located between the second distillation column (200) and the phase separator (40), where the remaining portion of the second bottom flow ($F_{2btm}$) may flow into the phase separator (40) after being introduced into the cooling device (70) and cooled. By lowering the temperature of the second bottom flow ($F_{2btm}$) and introducing it into the phase separator (40), the removal efficiency of methanol can be maximized.

In one example, the temperature of the second bottom flow ($F_{2btm}$) being cooled and introduced into the phase separator (40) may be 50 to 90° C., but is not limited thereto.

Hereinafter, the process of separating acetone and methanol with the distillation device according to one embodiment of the present application will be described in more detail.

In one example, when the feedstock ($F_1$) containing acetone, methanol and water flows into the first distillation column (100), in this case, a flow that acetone is rich, which is a relatively low boiling point component among components contained in the feedstock ($F_1$) introduced into the first distillation column (100), may flow out of the top region of the first distillation column (100) as the first top flow ($F_{1top}$), and a flow that methanol and water are rich, which are relatively high boiling point components, may flow out of the bottom region of the first distillation column (100) as the first bottom flow ($F_{1btm}$). The first top flow ($F_{1top}$) discharged from the top region of the first distillation column (100) passes through the first condenser (110) and is refluxed to the top region of the first distillation column (100), and the remaining portion may be stored as a product. The product may be highly pure acetone. The first top flow ($F_{1top}$) may comprise some methanol in addition to acetone, and as described above, in the first top flow ($F_{1top}$), the content of methanol may be 0.002 to 0.1 parts by weight relative to 100 parts by weight of the total components contained in the first top flow ($F_{1top}$).

Furthermore, a portion of the first bottom flow ($F_{1btm}$) discharged from the bottom region of the first distillation column (100) passes through the first reboiler (120), and a portion may be refluxed to the bottom region of the first distillation column (100) and the remaining portion may flow into the second distillation column (200). In addition, a flow that methanol is rich, which is a relatively low boiling point component among components contained in the feedstock flow ($F_2$) introduced into the second distillation column (200), may flow out of the top region of the distillation column (200) as the second top flow ($F_{2top}$), and a flow that cumene is rich, which has a relatively high boiling point, may flow out of the bottom region of the second distillation column (200) as the second bottom flow ($F_{2btm}$). The discharged second top flow ($F_{2top}$) passes through the second condenser (210) and flows into the storage tank, and a portion of the flow discharged from the storage tank may be refluxed to the top region of the second distillation column (200) and the remaining portion may be stored as a product. The product may be highly pure methanol. In addition, the high boiling point flow having a relatively high boiling point among the components contained in the flow introduced into the second distillation column (200) flows out of the bottom region of the second distillation column (200) as the second bottom flow ($F_{2btm}$), and a portion of the second bottom flow ($F_{2btm}$) may be refluxed to the bottom region of the second distillation column (200) via the second reboiler (220) and the remaining portion may flow into the phase separator (40).

In the second bottom flow ($F_{2btm}$) introduced into the phase separator (40), a small amount of acetone and methanol is contained and in addition to this, a component having a boiling point higher than that of methanol such as water, alpha-methylstyrene, and cumene may be contained in a higher concentration. In the phase separator (40), the components may be divided into a water-containing component ($F_{aqu}$) and an organic substance-containing component ($F_{org}$) and discharged. For example, among the above components, water and a small amount of acetone and methanol may be separated as a water-containing component ($F_{aqu}$) and discharged, and alpha-methylstyrene and cumene may be separated as an organic substance-containing component ($F_{org}$) and discharged.

The separated water-containing component ($F_{aqu}$) flows into the neutralizer (60) and reactants discharged from the reactor (50) in which the oxidation reaction of cumene occurs, for example, components comprising water, acetone, methanol, cumene and alpha-methylstyrene, etc., flow into the neutralizer (60) together. The components neutralized in the neutralizer (60) may be discharged and introduced into the third distillation column (300). The flow that acetone is rich, which is a relatively low boiling point component among the components contained in the flow ($F_3$) introduced into the third distillation column (300), flows out of the top region of the third distillation column (300) as the third top flow ($F_{3top}$), and the third top flow ($F_{3top}$) discharged from the top region of the third distillation column (300) may be refluxed to the top region of the third distillation column (300) via the third condenser (310) and the remaining portion may flow into the first distillation column (100). In addition, the high boiling point flow having a relatively high boiling point among the components contained in the flow ($F_3$) introduced into the third distillation column (300) flows out of the bottom region of the third distillation column (300) as the third bottom flow ($F_{3btm}$), and a portion of the third bottom flow ($F_{3btm}$) may be refluxed to the bottom region of the third distillation column (300) via the third reboiler (320) and the remaining portion may be stored as a product.

The flow introduced into the first distillation column (100), as described above, may be separated as the first top flow ($F_{1top}$) discharged from the top of the distillation column and discharged, and a portion of the first column flow ($F_{1top}$) may be circulated to the above described reactor (50).

In the present specification, the "low boiling point flow" means a flow in which a relatively low boiling point component is rich in a feedstock flow comprising low boiling point and high boiling point components, and the low boiling point flow means, for example, a flow discharged from each top region of the first distillation column (100), the second distillation column (200) and the third distillation column (300). Also, the "high boiling point flow" means a flow in which a relatively high boiling point component is rich in the feedstock flow comprising low boiling point and high boiling point components, and the high boiling point flow means, for example, a flow, in which the relatively high boiling point component is rich, discharged from each bottom region of the first distillation column (100), the second distillation column (200) and the third distillation column (300). The term "rich flow" above means a flow that each content of the low boiling point component contained in the flow discharged from each top region of the first distillation column (100), the second distillation column (200) and the third distillation column (300) and the high boiling point component contained in the flow discharged from each bottom region of the first distillation column (100), the second distillation column (200) and the third distillation column (300) is higher than each content of the low boiling point component and the high boiling point component contained in the feedstocks introduced into the first distillation column (100), the second distillation column (200) and the third distillation column (300), respectively. For example, it may mean a flow that each content represented by the low boiling point component contained in the first top flow ($F_{1top}$) of the first distillation column (100), the low boiling point component contained in the second top flow ($F_{2top}$) of the second distillation column (200) and the low boiling point component contained in the third top flow ($F_{3top}$) of the third distillation column (300) is at least 50% by weight, at least 80% by weight, at least 90% by weight, at least 95% by weight or at least 99% by weight or a flow that each content represented by the high boiling point component contained in the first bottom flow ($F_{1btm}$) of the first distillation column (100), the high boiling point component contained in the second bottom flow ($F_{2btm}$) of the second distillation column (200) and the high boiling point component contained in the third bottom flow ($F_{3btm}$) of the third distillation column (300) is at least 50% by weight, at least 80% by weight, at least 90% by weight, at least 95% by weight, or at least 99% by weight.

The present application also provides a distillation method. An exemplary distillation method by one embodiment of the present application may be performed by using the distillation device of FIG. 1 or FIG. 8 as described above, and therefore, the description overlapping with the contents described in the above-mentioned distillation device will be omitted.

The production method of the present application comprises a first distillation step, a second distillation step and a phase separation step.

In one embodiment, the first distillation step comprises i) introducing a feedstock ($F_1$) comprising a first compound, a second compound being capable of forming an azeotrope with the first compound and water into the first distillation column (100) and ii) dividing the feedstock introduced into the first distillation column (100), into a first top flow ($F_{1top}$) discharged from the top region of the first distillation column (100) and a first bottom flow ($F_{1btm}$) discharged from the bottom region of the first distillation column (100), respectively, and discharging them. In addition, the second distillation step comprises iii) introducing a portion of the first bottom flow ($F_{1btm}$) into the second distillation column (200) and iv) dividing a flow ($F_2$) introduced into the second distillation column (200), into a second top flow ($F_{2top}$) discharged from the top region of the second distillation column (200) and a second bottom flow ($F_{2btm}$) discharged from the bottom region of the second distillation column (200), respectively, and discharging them, and the phase separation step comprises v) introducing a portion of the second bottom flow ($F_{2btm}$) into the phase separator (40) and vi) dividing the flow introduced into the phase separator (40) into an organic substance-containing component ($F_{org}$) and a water-containing component ($F_{aqu}$), respectively, and discharging them.

Since steps i) and ii) of the first distillation step, steps iii) and iv) of the second distillation step, and steps v) and vi) of the phase separation step are each independently organically bonded, each boundary is not clearly divided according to the order of time, and thus the respective steps of i) to vi) may be performed sequentially or each independently at the same time.

In one embodiment, the first top flow ($F_{1top}$) comprises the first compound and the second compound, the first bottom flow ($F_{1btm}$) comprises the first compound, the second compound and a substance having a boiling point higher than that of the second compound, the second top flow ($F_{2top}$) comprises the first compound and the second compound, and the second bottom flow ($F_{2btm}$) comprises a substance having a boiling point higher than that of the second compound, and the specific description thereof will be omitted because it is the same as that described in the above-mentioned distillation device.

In addition, the content of the second compound in the first top flow ($F_{1top}$) may be 0.002 to 0.1 parts by weight relative to 100 parts by weight of the total components contained in the first top flow ($F_{1top}$). By controlling the content of the second compound in the first top flow ($F_{1top}$) within the above range, an accumulating amount of the second compound in the process can be minimized, whereby the second compound may be separated in high purity and the energy saving effect may be maximized.

In one example, when the content of the second compound in the first top flow ($F_{1top}$) of the first distillation column (100) is controlled within the above range, the content of the second compound in the second top flow stream ($F_{2top}$) of the second distillation column (200) may be 0.01 to 0.5 parts by weight relative to 100 parts by weight of the total components contained in the second top flow ($F_{2top}$).

In another embodiment, the distillation method of the present application may further comprise a cooling step. In one example, the distillation method may further comprise a cooling step to cool a portion of the second bottom flow ($F_{2btm}$) before introducing it into the phase separator (40). Accordingly, by lowering the temperature of the second bottom flow ($F_{2btm}$) and introducing it into the phase separator (40), the removal efficiency of methanol can be maximized.

In one example, the temperature of the second bottom flow ($F_{2btm}$) cooled in the cooling step may be 50 to 90° C., but is not limited thereto.

In addition, other embodiments of the present application also provide operating conditions of the second distillation step for increasing more the removal efficiency of methanol when performing the second distillation step between the first distillation step and the phase separation step as above.

In one example, the method may comprise adjusting the temperature of the top region of the second distillation column (200) to 40° C. to 120° C. In addition, the method may also comprise adjusting the pressure of the top region of the second distillation column (200) to −0.6 to 5.5 kgf/cm²g.

The method may also comprise adjusting the temperature of the bottom region of the second distillation column (200) to 70° C. to 160° C. The method may also comprise adjusting the pressure of the bottom region of the second distillation column (200) to −0.4 to 5.5 kgf/cm²g.

In one example, the first compound may be acetone, and in this case the second compound may be methanol, but is not limited thereto.

In addition, an exemplary distillation method of the present application may further comprise a neutralization step and a third distillation step.

In one embodiment, the neutralization step comprises introducing the water-containing component ($F_{aqu}$) discharged from the phase separator (40) and the feedstock containing the first compound and the second compound discharged from the reactor (50) into a neutralizer (60) to neutralize them. In addition, the third distillation step comprises introducing the feedstock comprising the first compound and the second compound, discharged from the neutralizer (60), into the third distillation column (300), and dividing the feedstock ($F_3$) introduced into the third distillation column, into the third top flow ($F_{3top}$) discharged from the top region of the third distillation column (300) and the third bottom flow ($F_{3btm}$) discharged from the bottom region of the third distillation column (300), respectively, and discharging them.

In this case, the distillation method of the present application comprises introducing a portion of the third top flow ($F_{3top}$) into the first distillation column (100) and introducing a portion of the first top flow ($F_{1top}$) into the reactor (50).

Another embodiment of the present application provides a distillation device.

FIG. 9 is a diagram schematically showing a distillation device according to another embodiment of the present application.

As in FIG. 9, the distillation device by one embodiment of the present application comprises a first distillation unit (10) comprising a first distillation column (100), a phase separator (40), and a second distillation unit (20) comprising a second distillation column (200) located at the posterior end of the phase separator (40) and fluidically connected to the phase separator (40).

In one embodiment, a feedstock ($F_1$) comprising a first compound, a second compound and water flows into the first distillation column (100) and the feedstock ($F_1$) comprising the first and second compounds and water, which is introduced into the first distillation column (100), is divided into a first top flow ($F_{1top}$) discharged from the top region of the first distillation column (100) and a first bottom flow ($F_{1btm}$) discharged from the bottom region of the first distillation column (100), respectively, and discharged. The first top flow ($F_{1top}$) discharged from the top region of the first distillation column (100) flows into the first condenser (110), and some or all of the first top flow ($F_{1top}$) passing through the first condenser (110) may be refluxed to the top region of the first distillation column (100) or stored as a product. In one example, the flow discharged from the first condenser (110) may be refluxed to the first distillation column (100) or stored as a product after being introduced into a storage tank and stored. In addition, a portion of the first bottom flow ($F_{1btm}$) discharged from the bottom region of the first distillation column (100) flows into the first reboiler (120), and a portion of the first bottom flow ($F_{1btm}$) passing through the first reboiler (120) may be refluxed to the bottom region of the first distillation column (100) and the remaining portion may flow into the second distillation column (200) to be described below.

In one embodiment, the first top flow ($F_{1top}$) comprises a relatively low boiling point component of the feedstock ($F_1$) components introduced into the first distillation column (100), and in one example, it comprises the first compound and the second compound. Also, the first bottom flow ($F_{1btm}$) comprises a relatively high boiling point component among the components contained in the feedstock ($F_1$) introduced into the first distillation column (100), and in one example, it comprises the first compound, the second compound and a substance having a boiling point higher than that of the second compound. In one example, as described above, the first compound may be acetone, and in this case, the second compound may be methanol and the substance having a boiling point higher than that of the second compound may comprise one or more selected from the group consisting of aliphatic aldehyde, alpha-methylstyrene, mesityl oxide and cumene, but is not limited thereto. In one embodiment, when the boiling point of the second compound is higher than the boiling point of the first compound, the first top flow ($F_{1top}$) may be a flow in which the concentration of the first compound is relatively higher than the concentration of the second compound, and the first bottom flow ($F_{1btm}$) may be a flow in which the concentration of the first compound is relatively lower than the concentration of the second compound.

It comprises the first compound, the second compound and a substance having a boiling point higher than that of the second compound, and the remaining portion of the first bottom flow ($F_{1btm}$) discharged from the bottom region of the first distillation column (100) may flow into the phase separator (40).

The flow introduced into the phase separator (40) can be phase separated in the phase separator (40), and in one example, it can be divided into an organic substance-containing component ($F_{org}$) and a water-containing component ($F_{aqu}$), respectively, and discharged. The organic substance-containing component ($F_{org}$) may comprise an organic component such as, for example, aliphatic aldehyde, alpha-methylstyrene, mesityl oxide or cumene as the remaining components, other than water, among the substances having a boiling point higher than that of the second compound, and the water-containing component ($F_{aqu}$) comprises water and may comprise a first compound and a second compound, for example, a small amount of acetone and methanol. The water-containing component ($F_{aqu}$) may be circulated to the first distillation column (100) through a neutralizer (60) and a third distillation unit (30), which are described below, and through such a process, the acetone product can be obtained in high purity.

In one example, the water-containing component ($F_{aqu}$) may flow into the second distillation column (200). In addition, the flow ($F_2$) introduced into the second distillation column (200) may be divided into the second top flow ($F_{2top}$) discharged from the top region of the second distillation column (200) and the second bottom flow ($F_{2btm}$) discharged from the bottom region of the second distillation column, respectively, and discharged.

The second top flow ($F_{2top}$) discharged from the top region of the second distillation column (200) flows into the second condenser (210), and some or all of the second top flow ($F_{2top}$) passing through the second condenser (210) may be refluxed to the top region of the second distillation column (200) or stored as a product. In one example, the flow discharged from the second condenser (210) may be refluxed to the second distillation column (200) or stored as a product after being introduced into the storage tank and stored. In addition, a portion of the second bottom flow ($F_{2btm}$) discharged from the bottom region of the second distillation column (200) flows into the second reboiler (220) and a portion of the second bottom flow ($F_{2btm}$) passing through the second reboiler (220) may be refluxed to the bottom region of the second distillation column (200).

The second top flow ($F_{2top}$) comprises relatively low boiling point components, for example, a first compound and a second compound, among components contained in the water-containing component ($F_{aqu}$) introduced into the second distillation column (200), and in one example, it may comprise one or more selected from the group consisting of acetone, methanol and water, but is not limited thereto. In addition, the second bottom flow ($F_{2btm}$) comprises a relatively high boiling point component, for example, a substance having a boiling point higher than that of the second compound, among components contained in the water-containing component ($F_{aqu}$) introduced into the second distillation column (200) and in one example, it may comprise water, but is not limited thereto.

When the second distillation column (200) is located at the posterior end of the phase separator (40) as above, the operating conditions inside the second distillation column (200) are adjusted as follows, whereby methanol may be removed with good efficiency.

In one example, the temperature of the top region of the second distillation column (200) may be 40° C. to 80° C., for example, 40° C. to 50° C. The temperature of the bottom region of the second distillation column (200) may be 80° C. to 120° C., for example, 80° C. to 100° C.

Furthermore, in this case, the pressure of the top region of the second distillation column (200) may be −0.6 to 5.5 kgf/cm²g. In addition, the pressure of the bottom region of the second distillation column (200) may be −0.4 to 5.5 kgf/cm²g.

In the distillation device of the present application, as described above, when the second compound is separated from the feedstock containing the first and second compounds being capable of forming an azeotrope and water, the content of the second compound in a flow discharged from the top of the first distillation column (100) can be minimized by installing the second distillation column (200) at a position for relatively separating the second compound easily, that is, at the posterior end of the phase separator (40) and separating the second compound from the second distillation column (200), followed by circulating it to the first distillation column (100). In one example, the content of the second compound in the first top flow ($F_{1top}$) may be 0.002 to 0.1 parts by weight relative to 100 parts by weight of the total components contained in the first top flow ($F_{1top}$). By controlling the content of the second compound in the first top flow ($F_{1top}$) within the above range, an accumulating amount of the second compound in the process can be minimized, whereby the second compound may be separated in high purity and the energy saving effect may be maximized.

In one example, when the content of the second compound in the first top flow ($F_{1top}$) of the first distillation column (100) is controlled within the above range, the content of the second compound in the second top flow ($F_{2top}$) of the second distillation column (200) may be 0.01 to 0.5 parts by weight relative to 100 parts by weight of the total components contained in the second top flow ($F_{2top}$).

As in FIG. 9, the distillation device of the present application may further comprise a reactor (50), a neutralizer (60) and a third distillation unit (30), in addition to the first distillation unit (10), the second distillation unit (20) and the phase separator (40) as described above. The third distillation unit (30) comprises a third condenser (310), a third reboiler (320) and a third distillation column (300), and since the contents related to the condenser, the reboiler and the distillation column are the same as described above, they are omitted.

The reactor (50) is a device in which a chemical reaction takes place, and the first compound and the second compound, which are generated as by-products of the chemical reaction, may flow out of the reactor (50). When the reaction occurring in the reactor (50) is, for example, an oxidation reaction of cumene, the first compound may be acetone and the second compound may be methanol. The first compound and the second compound, discharged from the reactor (50), may flow into the neutralizer (60) after being combined with the remaining portion of the second bottom flow ($F_{2btm}$) comprising a substance having a boiling point higher than that of the second compound, for example, water.

The neutralizer (60) is a device for neutralizing a feedstock containing the first compound, the second compound and water, in which the neutralization can avoid from corrosion in devices. The flow of the feedstock discharged after being neutralized in the neutralizer (60) may flow into the third distillation column (300) included in the third distillation unit (30).

In one example, the feedstock ($F_3$) introduced into the third distillation column (300) may be divided into the third top flow ($F_{3top}$) discharged from the top region of the third distillation column (300) and the third bottom flow ($F_{3btm}$) discharged from the bottom region of the third distillation column (300), respectively, and discharged.

The third top flow ($F_{3top}$) discharged from the top region of the third distillation column (300) flows into the third condenser (310), and some or all of the third top flow ($F_{3top}$) passing through the third condenser (310) may be refluxed to the top region of the third distillation column (300) or stored as a product. In one example, the flow discharged from the third condenser (310) may be refluxed to the third distillation column (300) or stored as a product after being introduced into the storage tank and stored. In addition, a portion of the third bottom flow ($F_{3btm}$) discharged from the bottom region of the third distillation column (300) flows into the third reboiler (320), and a portion of the third bottom flow ($F_{3btm}$) passing through the third reboiler (320) may be refluxed to the bottom region of the third distillation column (300) and the remaining portion may flow into the first distillation column (100) described above. Also, in this case, a portion of the first top flow ($F_{1top}$) may be introduced into the reactor (50) and circulated.

In another embodiment, the distillation device of the present application may further comprise a cooling device (70). FIG. 10 is a diagram schematically showing a distillation device according to an embodiment of the present application.

In one example, as in FIG. 10, the distillation device may further comprise a cooling device (70) located between the first distillation column (100) and the phase separator (40), where the remaining portion of the first bottom flow ($F_{1btm}$) may flow into the phase separator (40) after being introduced into the cooling device (70) and cooled. By lowering the temperature of the first bottom flow ($F_{1btm}$) and introducing it into the phase separator (40), the removal efficiency of methanol can be maximized.

In one example, the temperature of the first bottom flow ($F_{1btm}$) being cooled and introduced into the phase separator (40) may be 50 to 90° C., but is not limited thereto.

Hereinafter, the process of separating acetone and methanol using the distillation device according to one embodiment of the present application will be described in more detail.

In one example, when the feedstock ($F_1$) containing acetone, methanol and water flows into the first distillation column (100), in this case, a flow that acetone is rich, which is a relatively low boiling point component among components contained in the feedstock ($F_1$) introduced into the first distillation column (100), may flow out of the top region of the first distillation column (100) as the first top flow ($F_{1top}$), and a flow that methanol and water are rich, which are relatively high boiling point components, may flow out of the bottom region of the first distillation column (100) as the first bottom flow ($F_{1btm}$). The first top flow ($F_{1top}$) discharged from the top region of the first distillation column (100) passes through the first condenser (110) and is refluxed to the top region of the first distillation column (100), and the remaining portion may be stored as a product. The product may be highly pure acetone. The first top flow ($F_{1top}$) may comprise some methanol in addition to acetone, and as described above, in the first top flow ($F_{1top}$), the content of methanol may be 0.002 to 0.1 parts by weight relative to 100 parts by weight of the total components contained in the first top flow ($F_{1top}$).

Furthermore, a portion of the first bottom flow ($F_{1btm}$) discharged from the bottom region of the first distillation column (100) passes through the first reboiler (120), and a portion may be refluxed to the bottom region of the first distillation column (100) and the remaining portion may flow into the phase separator (40).

In the first bottom flow ($F_{1btm}$) introduced into the phase separator (40), methanol and a small amount of acetone are contained and in addition to this, a component having a boiling point higher than that of methanol such as water, alpha-methylstyrene, and cumene may be contained in a higher concentration. In the phase separator (40), the components may be divided into a water-containing component ($F_{aqu}$) and an organic substance-containing component ($F_{org}$) and discharged. For example, among the above components, water and methanol and a small amount of acetone may be separated as a water-containing component ($F_{aqu}$) and discharged, and alpha-methylstyrene and cumene may be separated as an organic substance-containing component ($F_{org}$) and discharged.

The separated water-containing component ($F_{aqu}$) flows into the second distillation column (200), and also, a flow that methanol is rich, which is a relatively low boiling point component among components contained in the feedstock flow ($F_2$) introduced into the second distillation column (200), may flow out of the top region of the distillation column (200) as the second top flow ($F_{2top}$), and a flow that cumene is rich, which has a relatively high boiling point, may flow out of the bottom region of the second distillation column (200) as the second bottom flow ($F_{2btm}$). The discharged second top flow ($F_{2top}$) passes through the second condenser (210) and flows into the storage tank, and a portion of the flow discharged from the storage tank may be refluxed to the top region of the second distillation column (200) and the remaining portion may be stored as a product. The product may be highly pure methanol. In addition, the high boiling point flow having a relatively high boiling point among the components contained in the flow ($F_2$) introduced into the second distillation column (200) flows out of the bottom region of the second distillation column (200) as the second bottom flow ($F_{2btm}$), and a portion of the second bottom flow ($F_{2btm}$) may be refluxed to the bottom region of the second distillation column (200) via the second reboiler (220) and the remaining portion may flow into the neutralizer (60).

Reactants discharged from the reactor (50) in which the oxidation reaction of cumene occurs, for example, components comprising water, acetone, methanol, cumene and alpha-methylstyrene, etc., flow into the neutralizer (60) together. The components neutralized in the neutralizer (60) may be discharged and introduced into the third distillation column (300). The flow that acetone is rich, which is a relatively low boiling point component among the components contained in the flow ($F_3$) introduced into the third distillation column (300), flows out of the top region of the third distillation column (300) as the third top flow ($F_{3top}$), and the third top flow ($F_{3top}$) discharged from the top region of the third distillation column (300) may be refluxed to the top region of the third distillation column (300) via the third condenser (310) and the remaining portion may flow into the first distillation column (100). In addition, the high boiling point flow having a relatively high boiling point among the components contained in the flow ($F_3$) introduced into the third distillation column (300) flows out of the bottom region of the third distillation column (300) as the third bottom flow ($F_{3btm}$), and a portion of the third bottom flow ($F_{3btm}$) may be refluxed to the bottom region of the third distillation column (300) via the third reboiler (320) and the remaining portion may be stored as a product.

The flow introduced into the first distillation column (100), as described above, may be separated as the first top flow ($F_{1top}$) discharged from the top of the distillation column and discharged, and a portion of the first column flow ($F_{1top}$) may be circulated to the above described reactor (50).

The present application also provides a distillation method. An exemplary distillation method by one embodiment of the present application may be performed by using the distillation device of FIG. 9 or FIG. 10 as described above, and therefore, the description overlapping with the contents described in the above-mentioned distillation device will be omitted.

The production process of the present application comprises a first distillation step, a phase separation step and a second distillation step.

In one embodiment, the first distillation step comprises i) introducing a feedstock ($F_1$) comprising a first compound, a second compound being capable of forming an azeotrope with the first compound and water into the first distillation column (100) and ii) dividing the feedstock introduced into the first distillation column (100), into a first top flow ($F_{1top}$) discharged from the top region of the first distillation column (100) and a first bottom flow ($F_{1btm}$) discharged from the bottom region of the first distillation column (100), respectively, and discharging them. In addition, the phase separation step comprises iii) introducing a portion of the first bottom flow ($F_{1btm}$) into the phase separator (40) and iv) dividing the flow introduced into the phase separator (40) into an organic substance-containing component ($F_{org}$) and a water-containing component ($F_{aqu}$), respectively, and discharging them, and the second distillation step comprises v) introducing the water-containing component ($F_{aqu}$) into the second distillation column (200) and vi) dividing a flow ($F_2$) introduced into the second distillation column (200), into a second top flow ($F_{2top}$) discharged from the top region of the second distillation column (200) and a second bottom flow ($F_{2btm}$) discharged from the bottom region of the second distillation column (200), respectively, and discharging them.

In addition, in the distillation method of the present application, when the second distillation step is performed after the phase separation step as above, the method comprises adjusting operating conditions inside the second distillation column (200) as follows, whereby methanol may be removed with good efficiency.

In one example, the method may comprise adjusting the temperature of the top region of the second distillation column (200) to 40° C. to 80° C., for example, 40° C. to 50° C. The method may also comprise adjusting the temperature of the bottom region of the second distillation column (200) to 80° C. to 120° C., for example, 80° C. to 100° C.

The method may comprise adjusting the pressure of the top region of the second distillation column (200) to −0.6 to 5.5 kgf/cm²g. In addition, the method may comprise adjusting the pressure of the bottom region of the second distillation column (200) to −0.4 to 5.5 kgf/cm²g.

Since steps i) and ii) of the first distillation step, steps iii) and iv) of the phase separation step, and steps v) and vi) of the second distillation step are each independently organically bonded, each boundary is not clearly divided according to the order of time, and thus the respective steps of i) to vi) may be performed sequentially or each independently at the same time.

In one embodiment, the first top flow ($F_{1top}$) comprises the first compound and the second compound, the first bottom flow ($F_{1btm}$) comprises the first compound, the second compound and a substance having a boiling point higher than that of the second compound, the second top flow ($F_{2top}$) comprises the first compound and the second compound, and the second bottom flow ($F_{2btm}$) comprises a substance having a boiling point higher than that of the second compound, and the specific description thereof will be omitted because it is the same as that described in the above-mentioned distillation device.

In addition, the content of the second compound in the first top flow ($F_{1top}$) may be 0.002 to 0.1 parts by weight relative to 100 parts by weight of the total components contained in the first top flow ($F_{1top}$). By controlling the content of the second compound in the first top flow ($F_{1top}$) within the above range, an accumulating amount of the second compound in the process can be minimized, whereby the second compound may be separated in high purity and the energy saving effect may be maximized.

In one example, when the content of the second compound in the first top flow ($F_{1top}$) of the first distillation column (100) is controlled within the above range, the content of the second compound in the second top flow stream ($F_{2top}$) of the second distillation column (200) may be 0.01 to 0.5 parts by weight relative to 100 parts by weight of the total components contained in the second top flow ($F_{2top}$).

In another embodiment, the distillation method of the present application may further comprise a cooling step. In one example, the distillation method may further comprise a cooling step to cool a portion of the first bottom flow ($F_{1btm}$) before introducing it into the phase separator (40). Accordingly, by lowering the temperature of the first bottom flow ($F_{1btm}$) and introducing it into the phase separator (40), the removal efficiency of methanol can be maximized.

In one example, the temperature of the first bottom flow ($F_{1btm}$) cooled in the cooling step may be 50 to 90° C., but is not limited thereto.

In one example, the first compound may be acetone, and in this case, the second compound may be methanol, but is not limited thereto.

In addition, an exemplary distillation method of the present application may further comprise a neutralization step and a third distillation step.

In one embodiment, the neutralization step comprises introducing a portion of the second bottom flow ($F_{2btm}$) and the feedstock containing the first compound and the second compound discharged from the reactor (50) into a neutralizer (60) to neutralize them. In addition, the third distillation step comprises introducing the feedstock comprising the first compound and the second compound discharged from the neutralizer (60) into the third distillation column (300), and dividing the feedstock ($F_3$) introduced into the third distillation column (300), into the third top flow ($F_{3top}$) discharged from the top region of the third distillation column (300) and the third bottom flow ($F_{3btm}$) discharged from the bottom region of the third distillation column (300), respectively, and discharging them.

In this case, the distillation method of the present application comprises introducing a portion of the third top flow ($F_{3top}$) into the first distillation column (100) and introducing a portion of the first top flow ($F_{1top}$) into the reactor (50).

Advantageous Effects

According to the distillation device of the present application, when a feedstock containing acetone and methanol is separated using a distillation device, a methanol removal distillation column may be located at a position for easily separating methanol to solve a problem due to accumulation of methanol in the process and to lower the methanol content in the acetone product, and thus the lifetime of catalysts can be extended, and moreover, methanol can be removed with good efficiency from a flow of the lower part of the distillation column obtaining the final acetone product by using only the conventional phase separator and one methanol removal distillation column further installed, so that the acetone product obtained from the upper part of the distillation column obtaining the acetone product can be obtained in high purity and the operating cost and the equipment cost of equipments can be greatly reduced.

BRIEF DESCRIPTION OF DRAWINGS

FIG. 1 is a diagram schematically showing a distillation device according to one embodiment of the present application.

FIG. 2 is a Txy diagram of a mixture of acetone and methanol under a pressure of 1 $kgf/cm^2g$, and FIG. 3 is a Txy diagram of a mixture of acetone and methanol at a pressure of 10 $kgf/cm^2g$.

FIGS. 4 to 7 are Txy diagrams of a mixture of water and methanol under each pressure of 2 $kgf/cm^2g$, 1 $kgf/cm^2g$, 0 $kgf/cm^2g$ and −0.5 $kgf/cm^2g$.

FIG. 8 is a diagram schematically showing a distillation device according to another embodiment of the present application.

FIG. 9 is a diagram schematically showing a distillation device according to another embodiment of the present application.

FIG. 10 is a diagram schematically showing a distillation device according to another embodiment of the present application.

10: first distillation unit 100: first distillation column
110: first condenser 120: first reboiler
20: second distillation unit 200: second distillation column
210: second condenser 220: second reboiler
30: third distillation unit 300: second distillation column
310: third condenser 320: third reboiler
40: phase separator 50: reactor
60: neutralizer 70: cooling device
$F_1$: feedstock comprising a first compound, a second compound capable of forming an azeotrope with the first compound, and water
$F_{1top}$: first top flow $F_{1btm}$: first bottom flow
$F_2$: flow introduced into the second distillation column
$F_{2top}$: second top flow $F_{2btm}$: second bottom flow
$F_3$: feedstock comprising the first compound and the second compound discharged from the neutralizer
$F_{3top}$: third top flow $F_{3btm}$: third bottom flow
$F_{org}$: organic substance-containing component $F_{aqu}$: water-containing component

MODE FOR INVENTION

Hereinafter, the present invention will be described in more detail through Examples complying with the present invention and Comparative Examples uncomplying with the present invention, but the scope of the present invention is not limited by the proposed examples.

EXAMPLE 1

Acetone and methanol were separated using the distillation device of FIG. 8.

Specifically, a feedstock containing 55% by weight of acetone, 22% by weight of cumene, 4% by weight of alpha-methylstyrene, 0.03% by weight of methanol, and 0.14% by weight of a high boiling point component was introduced into the first distillation column having a number of theoretical stages of 65 at a temperature of 88° C. and a flow rate of 43,000 kg/hr.

The first top flow discharged from the top region of the first distillation column passed through the first condenser and a portion was refluxed to the top region of the first distillation column. The remaining portion of the first top flow was separated and stored as a product comprising 99.8% by weight of acetone and 0.02% by weight of methanol, and the first bottom flow discharged from the bottom region of the first distillation column passed through the first reboiler, and a portion was refluxed to the bottom region of the first distillation column and the remaining portion was introduced into the second distillation column. In this case, the operating pressure of the first distillation column top region was adjusted to −0.44 $kgf/cm^2g$, the operating temperature was adjusted to 40° C., the operating pressure of the first distillation column bottom region was adjusted to −0.12 $kgf/cm^2g$, and the operating temperature was adjusted to be 89° C.

Furthermore, the second top flow discharged from the top region of the second distillation column passed through the second condenser, and a portion was refluxed to the top region of the second distillation column and the remaining portion was separated as a product comprising 54% by weight of acetone and 2% by weight of methanol. A portion of the second bottom flow discharged from the bottom region of the second distillation column was refluxed to the bottom region of the second distillation column through the second reboiler and the remaining portion was cooled through the cooling device and then introduced into the phase separator. In this case, the operating pressure of the top region of the second distillation column was adjusted to 5 $kgf/cm^2g$, the operating temperature was adjusted to be 114.1° C., the operating pressure of the bottom region of the second distillation column was adjusted to 5.14 $kgf/cm^2g$, and the operating temperature was adjusted to be 136.5° C. Also, the second bottom flow cooled through the cooling device was introduced into the phase separator at a temperature of 52° C.

In the phase separator, an organic substance-containing component comprising 83% by weight of cumene and 17% by weight of alpha-methylstyrene and a water-containing component comprising 99% by weight of water, 0.0002% by weight of acetone and 0.0604% by weight of methanol were separated and discharged, and the water-containing component was introduced into the neutralizer and introduced into the third distillation column together with the reaction product of the cumene oxidation reactor introduced into the neutralizer.

In addition, the third top flow discharged from the top region of the third distillation column passed through the third condenser, and a portion was refluxed to the top region of the third distillation column and introduced into the first distillation column A portion of the third bottom flow discharged from the bottom region of the third distillation column was refluxed to the bottom region of the third distillation column via the third reboiler and the remaining portion was separated as a product comprising pure phenol. In this case, the operating pressure of the third distillation column was adjusted to 0.38 $kgf/cm^2g$, the operating temperature was adjusted to be 120° C., the operating pressure of the bottom of the third distillation column was adjusted to 0.82 $kgf/cm^2g$, and the operating temperature was adjusted to be 204° C.

Meanwhile, a portion of the first top flow of the first distillation column was circulated to the reactor.

In the case of separating acetone and methanol using the distillation device of Example 1, the operating conditions of the second distillation column, the heat quantity used in the second reboiler, and the removal rate of methanol were shown in Table 1 below.

EXAMPLE 2

Acetone and methanol were separated by the same method as Example 1, except that the operating conditions of the second distillation column were changed as in Table 1 below.

In the case of separating acetone and methanol using the distillation device of Example 2, the used amount of energy in first and second reboilers and the removal rate of methanol were shown in Table 1 below.

EXAMPLE 3

Acetone and methanol were separated using the distillation device of FIG. 9.

Specifically, a feedstock containing 55% by weight of acetone, 22% by weight of cumene, 4% by weight of alpha-methylstyrene, 0.03% by weight of methanol, and 0.14% by weight of a high boiling point component was introduced into the first distillation column having a number of theoretical stages of 65 at a temperature of 88° C. and a flow rate of 43,000 kg/hr.

The first top flow discharged from the top region of the first distillation column passed through the first condenser and a portion was refluxed to the top region of the first distillation column. The remaining portion of the first top flow was separated and stored as a product comprising 99.8% by weight of acetone and 0.02% by weight of methanol, and the first bottom flow discharged from the bottom region of the first distillation column passed through the first reboiler, and a portion was refluxed to the bottom region of the first distillation column and the remaining portion was introduced into the phase separator. In this case, the operating pressure of the first distillation column top region was adjusted to −0.44 kgf/cm²g, the operating temperature was adjusted to 40° C., the operating pressure of the first distillation column bottom region was adjusted to −0.12 kgf/cm²g, and the operating temperature was adjusted to be 89° C.

In the phase separator, an organic substance-containing component comprising 82% by weight of cumene and 17% by weight of alpha-methylstyrene and a water-containing component comprising 99% by weight of water, 0.2% by weight of acetone and 0.0643% by weight of methanol were separated and discharged, and the water-containing component was introduced into the second distillation column.

Furthermore, the second top flow ($F_{2top}$) discharged from the top region of the second distillation column passed through the second condenser, and a portion was refluxed to the top region of the second distillation column and the remaining portion was separated as a product comprising 50% by weight of acetone and 14% by weight of methanol. A portion of the second bottom flow discharged from the bottom region of the second distillation column was refluxed to the bottom region of the second distillation column through the second reboiler and the remaining portion was introduced into the neutralizer and introduced into the third distillation column together with the reaction product of the cumene oxidation reactor introduced into the neutralizer. In this case, the operating pressure of the top region of the second distillation column was adjusted to −0.4 kgf/cm²g, the operating temperature was adjusted to be 47.9° C., the operating pressure of the bottom region of the second distillation column was adjusted to −0.26 kgf/cm²g, and the operating temperature was adjusted to be 92.0° C.

The third top flow discharged from the top region of the third distillation column passed through the third condenser, and a portion was refluxed to the top region of the third distillation column and introduced into the first distillation column. A portion of the third bottom flow discharged from the bottom region of the third distillation column was refluxed to the bottom region of the third distillation column via the third reboiler and the remaining portion was separated as a product comprising pure phenol. In this case, the operating pressure of the third distillation column was adjusted to 0.38 kgf/cm²g, the operating temperature was adjusted to be 120° C., the operating pressure of the bottom of the third distillation column was adjusted to 0.82 kgf/cm²g, and the operating temperature was adjusted to be 204° C.

Meanwhile, a portion of the first top flow of the first distillation column was circulated to the reactor.

In the case of separating acetone and methanol using the distillation device of Example 3, the operating conditions of the second distillation column, the heat quantity used in the second reboiler, and the removal rate of methanol were shown in Table 1 below.

EXAMPLE 4

Acetone and methanol were separated using the distillation device of FIG. 10.

Specifically, a feedstock containing 55% by weight of acetone, 22% by weight of cumene, 4% by weight of alpha-methylstyrene, 0.03% by weight of methanol, and 0.14% by weight of a high boiling point component was introduced into the first distillation column having a number of theoretical stages of 65 at a temperature of 88° C. and a flow rate of 43,000 kg/hr.

The first top flow discharged from the top region of the first distillation column passed through the first condenser and a portion was refluxed to the top region of the first distillation column. The remaining portion of the first top flow was separated and stored as a product comprising 99.8% by weight of acetone and 0.02% by weight of methanol, and the first bottom flow discharged from the bottom region of the first distillation column passed through the first reboiler, and a portion was refluxed to the bottom region of the first distillation column and the remaining portion was cooled through the cooling device and then introduced into the phase separator. In this case, the operating pressure of the first distillation column top region was adjusted to −0.44 kgf/cm²g, the operating temperature was adjusted to 40° C., the operating pressure of the first distillation column bottom region was adjusted to −0.12 kgf/cm²g, and the operating temperature was adjusted to be 89° C. Also, the first bottom flow cooled through the cooling device was introduced into the phase separator at a temperature of 52° C.

In the phase separator, an organic substance-containing component comprising 82% by weight of cumene and 17% by weight of alpha-methylstyrene and a water-containing component comprising 99% by weight of water, 0.2% by weight of acetone and 0.0672% by weight of methanol were separated and discharged, and the water-containing component was introduced into the second distillation column.

Furthermore, the second top flow ($F_{2top}$) discharged from the top region of the second distillation column passed through the second condenser, and a portion was refluxed to the top region of the second distillation column and the remaining portion was separated as a product comprising 42% by weight of acetone and 11% by weight of methanol. A portion of the second bottom flow discharged from the bottom region of the second distillation column was refluxed to the bottom region of the second distillation column through the second reboiler and the remaining portion was introduced into the neutralizer and introduced into the third distillation column together with the reaction product of the cumene oxidation reactor introduced into the neutralizer. In this case, the operating pressure of the top region of the second distillation column was adjusted to −0.5 kgf/cm$^2$g, the operating temperature was adjusted to be 45.7° C., the operating pressure of the bottom region of the second distillation column was adjusted to −0.36 kgf/cm$^2$g, and the operating temperature was adjusted to be 88.3° C.

The third top flow discharged from the top region of the third distillation column passed through the third condenser (310), and a portion was refluxed to the top region of the third distillation column and introduced into the first distillation column. A portion of the third bottom flow discharged from the bottom region of the third distillation column was refluxed to the bottom region of the third distillation column via the third reboiler and the remaining portion was separated as a product comprising pure phenol. In this case, the operating pressure of the third distillation column was adjusted to 0.38 kgf/cm$^2$g, the operating temperature was adjusted to be 120° C., the operating pressure of the bottom of the third distillation column was adjusted to 0.82 kgf/cm$^2$g, and the operating temperature was adjusted to be 204° C.

Meanwhile, a portion of the first top flow of the first distillation column was circulated to the reactor.

In the case of separating acetone and methanol using the distillation device of Example 4, the operating conditions of the second distillation column, the heat quantity used in the second reboiler, and the removal rate of methanol were shown in Table 1 below.

COMPARATIVE EXAMPLE 1

Acetone and methanol were separated by the same method as Example 1, except that the remaining portion of the first bottom flow discharged from the bottom region of the first distillation column was directly introduced into the phase separator without passing through the second distillation column.

In the case of separating acetone and methanol using the distillation device of Comparative Example 1, the operating conditions of the second distillation column, the heat quantity used in the second reboiler, and the removal rate of methanol were shown in Table 1 below.

COMPARATIVE EXAMPLE 2

Acetone and methanol were separated by the same method as Example 3, except that the operating conditions of the second distillation column were changed as Table 1 below.

In the case of separating acetone and methanol using the distillation device of Comparative Example 2, the operating conditions of the second distillation column, the heat quantity used in the second reboiler, and the removal rate of methanol were shown in Table 1 below.

COMPARATIVE EXAMPLE 3

Acetone and methanol were separated by the same method as Example 4, except that the operating conditions of the second distillation column were changed as Table 1 below.

In the case of separating acetone and methanol using the distillation device of Comparative Example 3, the operating conditions of the second distillation column, the heat quantity used in the second reboiler, and the removal rate of methanol were shown in Table 1 below.

TABLE 1

|  | Example | | | | Comparative Example | | |
| --- | --- | --- | --- | --- | --- | --- | --- |
|  | 1 | 2 | 3 | 4 | 1 | 2 | 3 |
| Removal rate of methanol | 11% | 80% | 75% | 76% | — | 60% | 61% |
| Heat quantity used in the second reboiler (Gcal/hr) | 1.00 | 1.00 | 1.00 | 1.00 | — | 1.00 | 1.00 |
| Top pressure of the second distillation column (kgf/cm$^2$g) | 5.0 | −0.3 | −0.4 | −0.5 | — | 5.0 | 1.0 |
| Top temperature of the second distillation column (° C.) | 114.1 | 46.1 | 47.9 | 45.7 | — | 117.0 | 81.3 |
| Bottom pressure of the second distillation column (kgf/cm$^2$g) | 4.14 | −0.16 | −0.26 | −0.36 | — | 5.14 | 1.14 |
| Bottom temperature of the second distillation column (° C.) | 136.5 | 72.2 | 92 | 88.3 | — | 159.2 | 122.2 |

The invention claimed is:

1. A distillation device which comprises a first distillation unit comprising a first condenser, a first reboiler and a first distillation column; a phase separator; and a second distillation unit comprising a second condenser, a second reboiler and a second distillation column located between said first distillation column and said phase separator and fluidically connected to said first distillation column and said phase separator, wherein a feedstock comprising a first compound, a second compound being capable of forming an azeotrope with said first compound and water, flows into said first distillation column, and the feedstock introduced into said first distillation column is divided into a first top flow discharged from a top region of said first distillation column and a first bottom flow discharged from a bottom region of said first distillation column, respectively, and discharged, wherein said first top flow flows into said first condenser and some or all of the first top flow passing through said first condenser is refluxed to the top region of said first distillation column, and a portion of said first bottom flow flows into said first reboiler and a portion of said bottom flow passing through said first reboiler is refluxed to the bottom region of said first distillation column, wherein a remaining portion of said first bottom flow flows into said second distillation column, and the remaining portion of said first bottom flow introduced into said second distillation column is divided into a second top flow discharged from a top region of said second distillation column and a second bottom flow discharged from a bottom region of said second distillation column, respectively, and discharged, wherein said second top flow flows into said second condenser and some or all of the second top flow passing through said second condenser is refluxed to the top region of said second distillation column, and a portion of said second bottom flow flows into said second reboiler and a portion of said second bottom flow passing through said second reboiler is refluxed to the bottom region of said second distillation column, wherein a remaining portion of said second bottom flow flows into said phase separator, and the remaining portion of said second bottom flow introduced into said phase separator is divided into an organic substance-containing component and a water-containing component in said phase separator, and discharged, wherein said first top flow comprises the first compound and the second compound, and said first bottom flow comprises the first compound, the second compound, and a substance having a boiling point higher than that of said second compound, wherein said second top flow comprises the first compound and the second compound, and said second bottom flow comprises a substance having a boiling point higher than that of said second compound, wherein the content of said second compound in said first top flow is 0.002 to 0.1 parts by weight relative to 100 parts by weight of the total components contained in said first top flow, and wherein the first compound is acetone, wherein the second compound is methanol, wherein the distillation device further comprises a cooling device located between the second distillation column and the phase separator, wherein the remaining portion of the second bottom flow flows into said phase separator after being introduced into said cooling device and cooled, wherein a temperature of the top region of the second distillation column is 40 to 70° C. and a pressure of the top region of the second distillation column is from −0.6 to 0kgf/cm²g, and wherein a temperature of the bottom region of the second distillation column is 70 to 95° C. and a pressure of the bottom region of the second distillation column is −0.4 to 0kgf/cm²g.

2. The distillation device according to claim 1, wherein the content of said second compound in the second top flow is 0.01 to 0.5 parts by weight relative to 100 parts by weight of the total components contained in said second top flow.

3. The distillation device according to claim 1, wherein the temperature of the cooled second bottom flow introduced into the phase separator is 50 to 90° C.

4. The distillation device according to claim 1, wherein the organic substance-containing component comprises one or more selected from the group consisting of aliphatic aldehyde, alpha-methylstyrene, water and cumene.

5. The distillation device according to claim 1, wherein the water-containing component comprises the first compound, the second compound and water.

6. The distillation device according to claim 1, further comprising a reactor; a neutralizer; and a third distillation unit comprising a third condenser, a third reboiler and a third distillation column, wherein the water-containing component discharged from the phase separator and the feedstock containing the first compound and the second compound, discharged from said reactor, flow into the neutralizer, and the feedstock containing the first compound and the second compound discharged from the neutralizer flows into the third distillation column, wherein the feedstock introduced into said third distillation column is divided into a third top flow discharged from a top region of said third distillation column and a third bottom flow discharged from a bottom region of said third distillation column, respectively, and discharged, wherein said third top flow flows into said third condenser and a portion of the third top flow passing through said third condenser is refluxed to the top region of said third distillation column, and a portion of said third bottom flow flows into said third reboiler and a portion of said third bottom flow passing through said third reboiler is refluxed to the bottom region of said third distillation column, and wherein a remaining portion of said third top flow flows into the first distillation column, and a portion of the first top flow flows into said reactor.

* * * * *